United States Patent
Kahn

(10) Patent No.: US 7,025,781 B2
(45) Date of Patent: Apr. 11, 2006

(54) ARTIFICIAL IRIS DIAPHRAGM IMPLANT

(76) Inventor: Delary Alberto Kahn, P.O. Box 527948 B50053, Miami, FL (US) 33152

( * ) Notice: Subject to any disclaimer, the term of this patent is extended or adjusted under 35 U.S.C. 154(b) by 0 days.

(21) Appl. No.: 10/355,973

(22) Filed: Jan. 31, 2003

(65) Prior Publication Data

US 2004/0153148 A1 Aug. 5, 2004

(51) Int. Cl.
*A61F 2/14* (2006.01)
(52) U.S. Cl. ...................................................... 623/4.1
(58) Field of Classification Search ................ 623/4.1, 623/905, FOR 103, 6.17, 6.36
See application file for complete search history.

(56) References Cited

U.S. PATENT DOCUMENTS

| | | | |
|---|---|---|---|
| 4,715,373 A * | 12/1987 | Mazzocco et al. ........... | 606/107 |
| 4,725,277 A | 2/1988 | Bissonette | |
| 5,628,797 A | 5/1997 | Richer | |
| 6,083,261 A | 7/2000 | Callahan et al. ............. | 623/6.38 |
| 6,221,106 B1 | 4/2001 | Hermeking ................. | 623/6.4 |
| 6,224,628 B1 | 5/2001 | Callahan et al. ............. | 623/6.4 |
| 6,280,469 B1 | 8/2001 | Terry et al. .................. | 623/4.1 |
| 6,398,809 B1 | 6/2002 | Hoffmann et al. .......... | 623/6.49 |

FOREIGN PATENT DOCUMENTS

| | | |
|---|---|---|
| DE | 39 26 536 A1 * | 2/1991 |
| FR | 2 696 340 A1 * | 4/1994 |
| JP | 2002-360616 A * | 12/2002 |

OTHER PUBLICATIONS http://www.rmb.org.uk./info/coloboma.htm "Coloboma Fact Sheet" (Jun. 2002), 2 pages.
http//www.ophtec.com/_frame_tekst/product_line/irisreconstruction.htm (2002), 4 pages.
http://www.fovicare.com/lensmodels.htm "Focal Vision International" (2002), 2 pages.
http://www.lensmart.com/common/productlens.asp?prodid=50&referral=ivd1034& (2002), 3 pages.
Patel, N., et al. "Subluxated cataracts can be safely managed with capsular tension ring." Ocular Surgery News (2002).
http://www.osnsupersite.com/print.asp?id=2021&imgname=banners/alcon_neosonix2.gif, 5 pages.
Cassel, M. "Colored Lens Options 12 steps to successful prosthetic soft contact lens fitting." http://www.customcontacts.com/medhtml/medart.htm (2002), 5 pages.
de Brabander, J., et al. "The use of standard thin high water content artificial iris and black pupil contact lenses." http://www.djo.harvard.edu/debrabander/index.html (1995), 7 pages.

* cited by examiner

*Primary Examiner*—David H. Willse
(74) *Attorney, Agent, or Firm*—Ladas & Parry

(57) ABSTRACT

An artificial soft iris diaphragm implant comprising an internal medial opening and opaque artwork of selected desired colors resembling a natural iris. The implant is insertable into the anterior chamber of the eye for cosmetic and/or medical reasons. The implant has flap portions that are insertable into the angle recess in the anterior chamber and maintain the implant in position. The flap portions may preferably be thinner than a body portion of the implant. When inserted into the anterior chamber, neither the visual axis nor the natural pupil is disturbed.

20 Claims, 2 Drawing Sheets

ARTIFICIAL IRIS DIAPHRAGM IMPLANT

FIELD OF THE INVENTION

The present invention relates to eye implants and particularly to artificial iris implants and the method of using such implants. The present invention solves the need that exists to provide a natural cosmetic iris and pupil appearance in patients suffering from coloboma of the iris. Even if the natural iris is intact, it will be unaffected by the artificial iris of the present invention. The artificial iris of the present invention can also be used for cosmetic reasons, allowing altering of the appearance of the eye without the limitations of traditional contact lenses.

BACKGROUND OF THE INVENTION

The human eye is a complex optical system. Vision begins when light enters the eye through the cornea, the front clear "window" of the eye responsible for focusing light rays to the back of the eye. From there, it travels through clear aqueous fluid, and passes through a small aperture in the iris, the colored structure which rests behind the cornea and in front of the natural lens. The opening in the center of the iris is the pupil. The iris acts like a camera shutter and controls the amount of light that enters the eye. As muscles in the iris relax or constrict, the pupil changes size to adjust the amount of light entering the eye. Light rays are focused through the lens and proceed through a clear jelly-like substance in the center of the eye called vitreous, which gives it form and shape. When light rays finally land on the retina, the part of the eye similar to film in a camera, they form an upside-down image. The retina contains millions of photo-receptor cells which convert light into images. The retina converts the image into an electrical impulse that travels along the optic nerve to the brain, where it is interpreted as an upright image.

Usually resulting from unexplained birth defects, coloboma describes a situation where a portion of the structure of the eye is lacking. This gap can occur in a range of areas and can be large or small. It can appear as a black notch of varying depth at the edge of the pupil, giving the pupil an irregular shape. The most common form of gap is caused by an imperfect closure of a cleft, present in the womb but usually closed by birth date. This gap can occur in the eyelid, iris, lens, choroid or optic disc. This does not mean that there is a hole in the eye, just that certain structures within the eye do not fully form. Coloboma of the iris may sometimes give the appearance of a keyhole in the pupil.

Attempts have been made to address the problems affecting patients suffering from coloboma of the iris by providing iris reconstruction implants. However, the implants of the prior art have been complicated multiple-piece lens which are cumbersome and uncomfortable. The methods of implantation have required complicated implantation techniques. Certain of these implants and methods are discussed next.

U.S. Pat. No. 6,280,469 to Terry et al describes an implantable artificial iris device in the form of a thin, generally annular wafer or web that is colored to replicate the appearance of an iris. The device is implanted either within the region known as the ciliary sulcus or in the region of meeting or joinder of the anterior and posterior capsules and within the realm of the capsular bag. In either case, the method of implantation involves surgical trimming of the natural iris. Implantation is by way of "a circular threading (or snaking)" of the implants into the eye chambers.

U.S. Pat. No. 5,628,797 to Richer describes a cosmetic anterior chamber intraocular lens and implantation method, wherein the lens is a multiple-piece lens with a circular joint or hinge and locking latch. The patent describes the implantation of the lens with haptics, or lens support elements, which are provided for keeping the lens in position in "angle structures of the eye". The haptics, which are depicted schematically in the patent, must be "opened" after insertion into the anterior chamber to perform their function.

Although the haptics (or lens support elements) for use with the Richer implants are described only schematically in the patent, the prior art is replete with descriptions of haptics that may be used with ocular implants. By way of example, U.S. Pat. No. 6,224,628 to Callahan et al describes in the Background portion thereof a number of patents that have issued for these lens supporting elements. These patents, and the Callahan et al patent itself, describe haptics of a variety of shapes and geometries, all of which have drawbacks relating to their insertion, manufacture and/or use. In particular, the prior art haptics make the prior art implants employing the same more difficult to insert into the eye and, at least in certain instances, undesirable in use. What has been needed is an implant that can be used, for example, by patients suffering from coloboma of the iris and that is implantable in the eye of a patient in a simple and straightforward manner without the use of the complicated haptics of the prior art.

SUMMARY OF THE INVENTION

In accordance with the invention, there is provided an implant for insertion into the angle recess in the anterior chamber of an eye, the implant comprising: a diaphragm that is insertable into the anterior chamber to cover a natural iris of the eye. The diaphragm comprises a flexible and foldable material and has a main portion that defines a round opening in the center of the diaphragm. The material is opaque and has a color that imparts to at least the main portion the hue of an iris of a human eye. The diaphragm comprises flap means at a periphery thereof for insertion into the angle recess in the anterior chamber, and for maintaining the implant in position in the anterior chamber with the main portion covering the natural iris and with the opening being aligned with a pupil of the eye. The flap means comprises a plurality of flap portions or foot plates that protrude from the periphery, the periphery being otherwise circular. The flap portions are integrally formed with the main portion to provide the diaphragm with a unitary construction.

In a preferred embodiment of the invention, the material of the flap portions is thinner than the material of the body portion, and the flap portions are evenly spaced around the periphery of the diaphragm.

In another preferred embodiment, the main portion of the diaphragm may have a diameter of between about 11 and 13 mm, with the opening having a diameter of about 3 to 4 mm. The diaphragm may have a generally annular surface with the main portion having a vault height of about 0.4–0.6 mm. In a most preferred embodiment the main portion has a vault height of about 0.5 mm.

In another embodiment, the main portion of the diaphragm has a thickness of about 0.15–0.17 mm and each of the flap portions is thinner than the main portion, with a thickness of about 0.10–0.14 mm. In this embodiment, the flap portions are semicircular in shape and the implant comprises six evenly spaced flap portions. Preferably, the material of the implant is silicone of ophthalmic grade because of its elasticity, flexibility and proven biocompatibility. Other materials that have these properties, such as plastics or acrylics may also be used.

There is also provided in accordance with the invention a method for inserting and positioning an implant into the eye of a patient, the method comprising:

(a) providing the aforementioned implant;

(b) inserting the implant into the anterior chamber of the eye and positioning the flap portions at the angle recess in the anterior chamber. Since the implant is foldable and does not require complicated haptics, the implant may be folded and inserted into the eye through a surgical wound in the cornea that is not larger than 4 mm.

In accordance with a preferred embodiment of the method of the invention, the only manipulations that need be done for the insertion of the implant are: 1) making a small wound in the cornea; 2) folding the implant and inserting the implant through the wound into the anterior chamber; and 3) positioning the flap portions at the angle recess with the main portion of the diaphragm covering the natural iris of the patient and with the opening of the diaphragm aligned with the pupil of the patient's eye. Using this procedure, the corneal incision may be so small that sutures can be dispensed with.

As the detailed description which now follows below is read in conjunction with the accompanying drawings, other features and advantages of the proposed device will become more fully apparent, as will also the unique installation surgical methodology which it permits.

DETAILED DESCRIPTION OF THE PREFERRED EMBODIMENT

Figure 1:
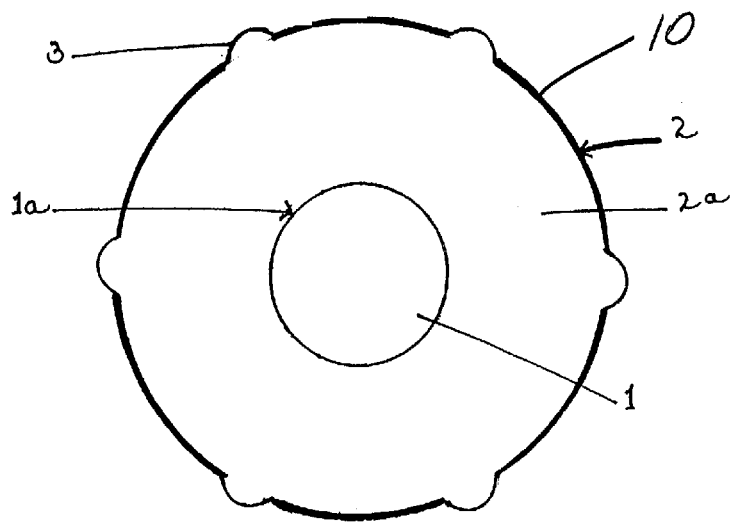
FIG. 1 is a plan frontal view of the artificial iris implant 2 of the present invention showing the medial opening 1 and supporting lids or flaps 3.

A preferred embodiment of the invention is now described in detail. Referring to the drawings, like numbers indicate like parts throughout the views. The system of the present invention comprises a unitary, one-piece artificial iris implant 2.

As shown in FIG. 1, the artificial soft iris implant 2, as for example made of silicone, comprises an internal, medial opening 1 extending through the implant from a first end to a second end of the implant (through its thickness). The medial opening is generally circular in shape having smooth borders 1a. The surrounding area around the medial opening 1 and extending to the peripheral edges of the artificial soft iris implant 2 is surface 2a. Surface 2a comprises opaque artwork of varying colors, the artwork resembling the artwork of a natural iris of the eye. The surface 2a is smooth, thus not affecting the natural movements of the natural iris and pupil. The peripheral edges of the artificial soft iris implant 2 comprise an outer thinner edge portion 2c and small supporting flaps or lids 3 which protrude from the edge portion 2c. In a preferred embodiment the lids 3 protrude between 0.3–0.7 mm and, in a most preferred embodiment, by not more than 0.5 mm. Supporting lids 3 are located symmetrically around the peripheral edge 10 of the implant 2 at, for example, the 1,3,5,7, 9 and 11 o'clock positions. The supporting lids 3 are generally arcuate in shape.

Figure 2:
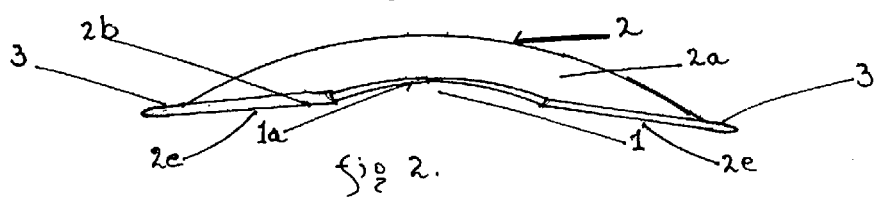
FIG. 2 is a side view of the artificial iris implant 2.

As shown in FIG. 2, artificial soft iris implant 2 is not flat but is a generally arcuate structure, having a vault height 2e. The implant 2 is provided with height 2e in order to be positioned in spaced relation from the natural iris, so that damage of the natural iris is avoided.

Figure 3:
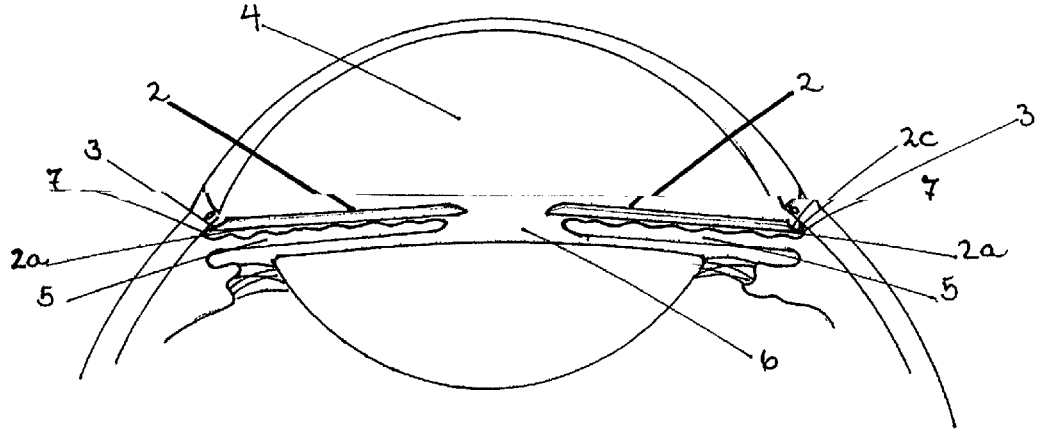
FIG. 3 is a schematic representation of the eye showing the positioning of the artificial iris implant 2 in the anterior chamber of the eye.

As can be seen in FIG. 3, the artificial soft iris implant 2 is introduced into the anterior chamber 4 of the eye, positioned above the natural iris 5 without interfering with the visual axis or with the natural pupil. The supporting lids 3 comprising the outer thinner portion 2c are located at a portion of the eye adjacent to the canal of schlemm, where there is a natural angle recess 7. This recess retains the implant in position after insertion into the anterior chamber, insuring a comfortable and secure fit for the user.

Figure 4:
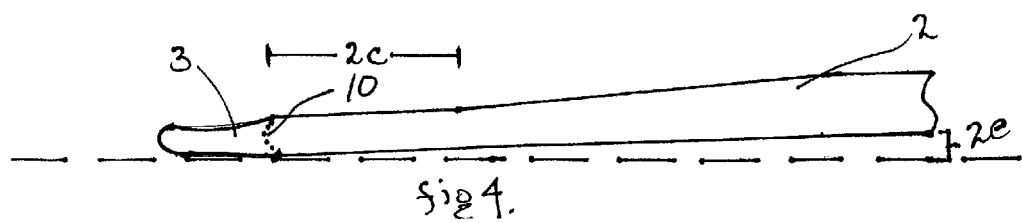
FIG. 4 is a partial view in cross section of a preferred artificial iris implant.

FIG. 4 shows a preferred embodiment of the invention which clearly shows that the thinner edge portion 2c with flaps or lids 3 tapers gradually toward the peripheral edge 10 (dotted line) of the implant with the flap or lid 3 being thinner still. The lids or flaps 3 are configured and positioned to function as stabilizers and positioners of the implant without significantly interfering with normal aqueous flow into or out of the anterior chamber. By contrast, a uniformly narrow implant periphery without lids could elevate the pressure in the eye and could possibly induce an iatrogenic angle closure glaucoma.

The invention is compatible with the latest improvements in lens implant techniques although serving different purposes as mentioned. Since the artificial soft iris diaphragm implant is foldable, only a 4 mm surgical wound in the cornea is necessary, thus achieving implantation without much surgical manipulation. Thus, implantation can be done in clear corneas, with no more than topical anesthesia and requiring no sutures. The implant is useful, novel, practical and cost effective, with reduction of surgical time, expensive materials and medications, as well as practically no physical restrictions post-operative, enabling an almost immediate return to daily life activities without undue pain or anxiety, these being important advantages to the user.

Example of Method of Insertion/Implantation of Diaphragm.

Figure 5:
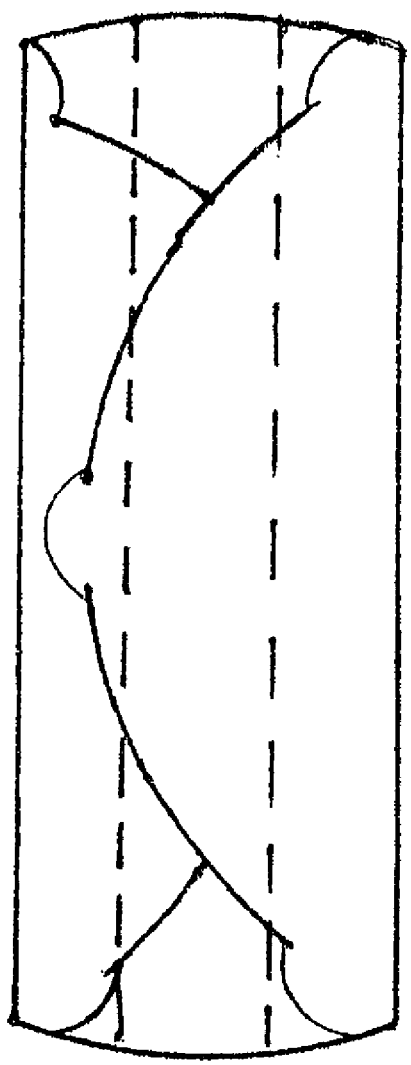
FIG. 5 shows the artificial iris in a rolled configuration for insertion into the anterior chamber of the eye.

Preparing the eye: The pupil is pharmacologically "closed" by means of topical Pilacarpine or alternatively intraocular miostatics (myochol or myostat). Under topical anesthesia, viscoelastic is introduced into the anterior chamber through a peripheral paracentesis in order to protect the endothelium, iris and lens and to assure a deep anterior chamber. A clear cornea self-sealing 3 mm peripheral incision is now created by means of a clear cornea tunnel incision blade. The implant may now be folded as follows: Using fine forceps, the external 3 o'clock border is gently grasped and rolled medially toward the central aperture; similarly the 9 o'clock border is also rolled medially (see FIG. 5). Both "rolls" are now pressed against each other using fine platform forceps while introducing the implant through the 3 mm incision (incision may be widened if needed) into the anterior chamber placing the aperture centrally and the flaps at the angle recess after gently being released. The implant is now in place and viscoelastic may be rinsed out. Sutures are not needed.

Although a preferred embodiment has been described, it is contemplated that various modifications and changes could be made without deviating from the spirit and scope of the present invention. Thus, it will be understood by those skilled in the art that the product and method illustrated and described herein is given by way of example only and may be varied widely within the scope of the appended claims.

What is claimed is:

1. An implant for insertion into the angle recess in the anterior chamber of an eye, the implant comprising: a diaphragm that is insertable into the anterior chamber to cover a natural iris of the eye, said diaphragm comprising a flexible and foldable material and having a main portion that defines a round opening in the center of the diaphragm, said material being opaque and having a color that imparts to at least the main portion the hue of an iris of a human eye; said diaphragm comprising flap means at a periphery thereof for insertion into the angle recess and for maintaining the implant in position in the anterior chamber with the main portion covering the natural iris and with the opening being aligned with a pupil of the eye, said flap means comprising a plurality of foot plates that consist of localized bulges that bulge from the periphery, wherein the bulges of the foot plates interrupt a circularity of the periphery, the periphery being otherwise circular, said foot plates being integrally formed with the main portion to provide the diaphragm with a unitary construction.

2. The implant according to claim 1, wherein the foot plates are thinner than the main portion.

3. The implant according to claim 1, wherein the foot plates are evenly spaced around the periphery of the diaphragm, and protrude from the periphery a distance of 0.3–0.7 mm.

4. The implant according to claim 3, wherein the main portion has a diameter of between about 11 and 13 mm, and the opening has a diameter of about 3 to 4 mm.

5. The implant according to claim 4, wherein the main portion has a vault height of about 0.4–0.6 mm.

6. The implant according to claim 5, wherein the foot plates protrude from the periphery by not more than 0.5 mm.

7. The implant according to claim 5, wherein the main portion has a thickness of about 0.15–0.17 mm and each of the flap portions is thinner than the main portion and protrudes from the periphery a distance of 0.3–0.7 mm.

8. The implant according to claim 7, wherein each of the foot plates has a thickness of about 0.10–0.14 mm.

9. The implant according to claim 7, wherein the foot plates are semicircular in shape.

10. The implant according to claim 9, wherein the flap means comprise six evenly spaced foot plates.

11. The implant according to claim 10, wherein the material is silicone.

12. The implant according to claim 1, wherein the main portion tapers toward the periphery such that a second portion of the main portion adjacent the periphery is thinner than a first portion of the main portion adjacent the round opening.

13. The implant according to claim 12, wherein the foot plates are thinner than the second portion of the main portion.

14. A method for inserting and positioning an implant into the eye of a patient, the method comprising:
   (a) providing the implant of claim 1;
   (b) rolling first and second borders of the diaphragm medially toward the center of the diaphragm to form two rolls and pressing the two rolls together; and
   (c) inserting the pressed rolls into the anterior chamber of the eye and releasing them so as to cause the foot plates to be positioned at the angle recess with the main portion of the diaphragm covering the natural iris of the patient and with the opening being aligned with the pupil of the patient.

15. The method according to claim 14, wherein the pressed rolls are inserted into the anterior chamber through an incision in the cornea of the eye that is 4 mm or smaller.

16. The method according to claim 14, wherein the method consists essentially of steps a, b and c.

17. A method for inserting and positioning an implant into the eye of a patient, the method comprising:
   (a) providing the implant of claim 2;
   (b) rolling first and second borders of the diaphragm medially toward the center of the diaphragm to form two rolls and pressing the two rolls together; and
   (c) inserting the pressed rolls into the anterior chamber of the eye and releasing them so as to cause the foot plates to be positioned at the angle recess with the main portion of the diaphragm covering the natural iris of the patient and with the opening being aligned with the pupil of the patient.

18. A method for inserting and positioning an implant into the eye of a patient, the method comprising:
   (a) providing the implant of claim 3;
   (b) rolling first and second borders of the diaphragm medially toward the center of the diaphragm to form two rolls and pressing the two rolls together; and
   (c) inserting the pressed rolls into the anterior chamber of the eye and releasing them so as to cause the foot plates to be positioned at the angle recess with the main portion of the diaphragm covering the natural iris of the patient and with the opening being aligned with the pupil of the patient.

19. A method for inserting and positioning an implant into the eye of a patient, the method comprising:
   (a) providing the implant of claim 7;
   (b) rolling first and second borders of the diaphragm medially toward the center of the diaphragm to form two rolls and pressing the two rolls together; and
   (c) inserting the pressed rolls into the anterior chamber of the eye and releasing them so as to cause the foot plates to be positioned at the angle recess with the main portion of the diaphragm covering the natural iris of the patient and with the opening being aligned with the pupil of the patient.

20. A method for inserting and positioning an implant into the eye of a patient, the method comprising:
   (a) providing the implant of claim 9;
   (b) rolling first and second borders of the diaphragm medially toward the center of the diaphragm to form two rolls and pressing the two rolls together; and
   (c) inserting the pressed rolls into the anterior chamber of the eye and releasing them so as to cause the foot plates to be positioned at the angle recess with the main portion of the diaphragm covering the natural iris of the patient and with the opening being aligned with the pupil of the patient.

* * * * *